(12) United States Patent
Liu

(10) Patent No.: US 11,345,563 B2
(45) Date of Patent: May 31, 2022

(54) FOLDING MACHINE FOR FOLDING FIBER PRODUCTS AND STACK OF FIBER PRODUCTS PRODUCED THEREBY

(71) Applicant: CHAN LI MACHINERY CO., LTD., Taoyuan (TW)

(72) Inventor: Wen-Cheng Liu, Taoyuan (TW)

(73) Assignee: CHAN LI MACHINERY CO., LTD., Taoywan (TW)

( * ) Notice: Subject to any disclaimer, the term of this patent is extended or adjusted under 35 U.S.C. 154(b) by 450 days.

(21) Appl. No.: 16/382,630

(22) Filed: Apr. 12, 2019

(65) Prior Publication Data

US 2020/0247639 A1    Aug. 6, 2020

(30) Foreign Application Priority Data

Feb. 1, 2019    (TW) ................................. 108104303

(51) Int. Cl.
| | | |
|---|---|---|
| *B65H 45/20* | (2006.01) | |
| *B65H 45/101* | (2006.01) | |
| *B65H 45/28* | (2006.01) | |
| *A61F 13/15* | (2006.01) | |
| *B41F 13/60* | (2006.01) | |
| *B41F 13/62* | (2006.01) | |
| *B41F 13/64* | (2006.01) | |
| *B65H 45/04* | (2006.01) | |

(52) U.S. Cl.
CPC ......... *B65H 45/20* (2013.01); *B65H 45/1015* (2013.01); *B65H 45/28* (2013.01); *A61F 13/15747* (2013.01); *B41F 13/60* (2013.01); *B41F 13/62* (2013.01); *B41F 13/64* (2013.01); *B65H 45/04* (2013.01)

(58) Field of Classification Search
CPC .... B65H 45/20; B65H 45/1015; B65H 45/28; B65H 45/04; B41F 13/60; B41F 13/62; B41F 13/64; A61F 13/15747
USPC ......................................................... 493/413
See application file for complete search history.

(56) References Cited

U.S. PATENT DOCUMENTS

| | | | | |
|---|---|---|---|---|
| 2009/0137375 | A1* | 5/2009 | Tsai ........................ | B31F 5/00 493/442 |
| 2016/0264373 | A1* | 9/2016 | Kauppila ............... | B65H 37/06 |
| 2019/0099974 | A1* | 4/2019 | Shin ....................... | B65H 45/28 |

* cited by examiner

*Primary Examiner* — Chelsea E Stinson
*Assistant Examiner* — Mary C Hibbert-Copeland
(74) *Attorney, Agent, or Firm* — Rosenberg, Klein & Lee

(57) ABSTRACT

A folding machine for folding fiber products and fiber products formed and stacked thereby are disclosed. The folding machine includes two folding devices, each of which includes a cutting device, a delivery wheel, a folding-line wheel, a platen wheel, and a folding wheel. The cutting device cuts the fiber product and transports the cut fiber product to the delivery wheel. The folding-line wheel is adjacent to the delivery wheel for making a first folding line on the fiber product carried by the delivery wheel, and then the platen wheel folds the fiber product along the first folding line. Subsequently, the once-folded fiber product is transported to the folding wheel. The folding wheels of the two folding devices are adjacent to each other and are used to fold the fiber product passing therethrough for a second time, and thus fiber products with three folds are formed.

8 Claims, 12 Drawing Sheets

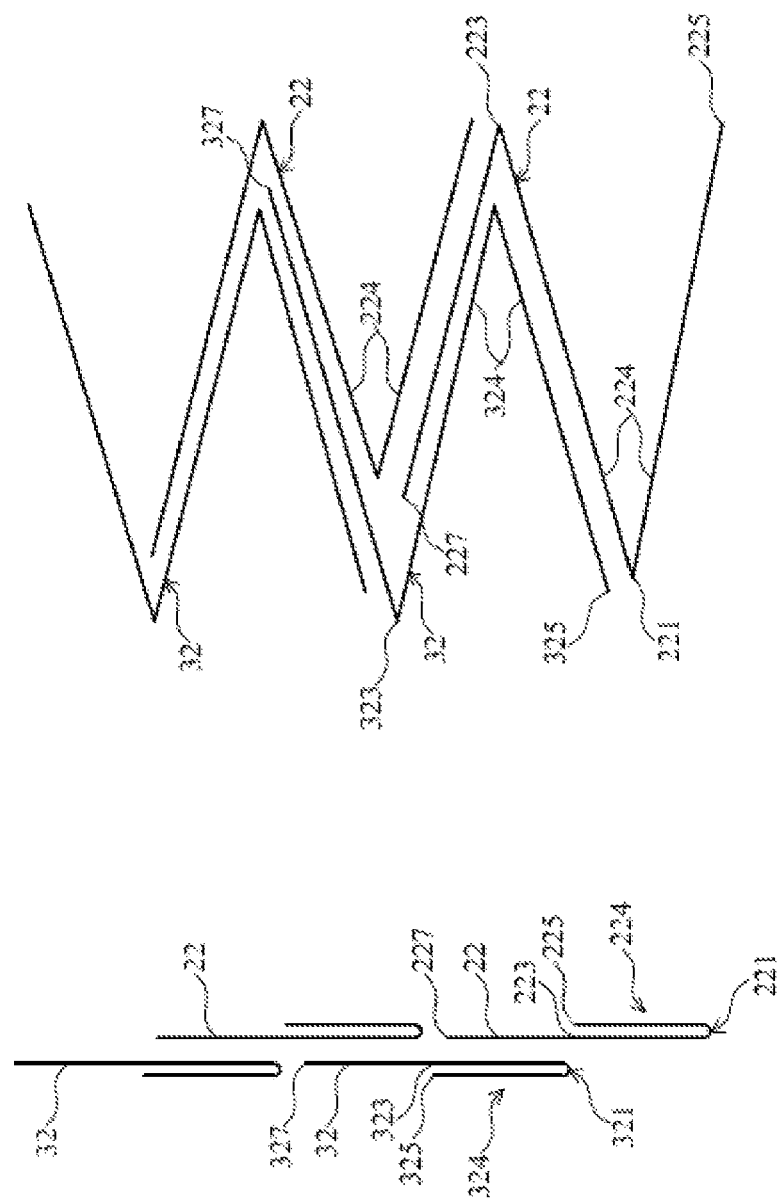

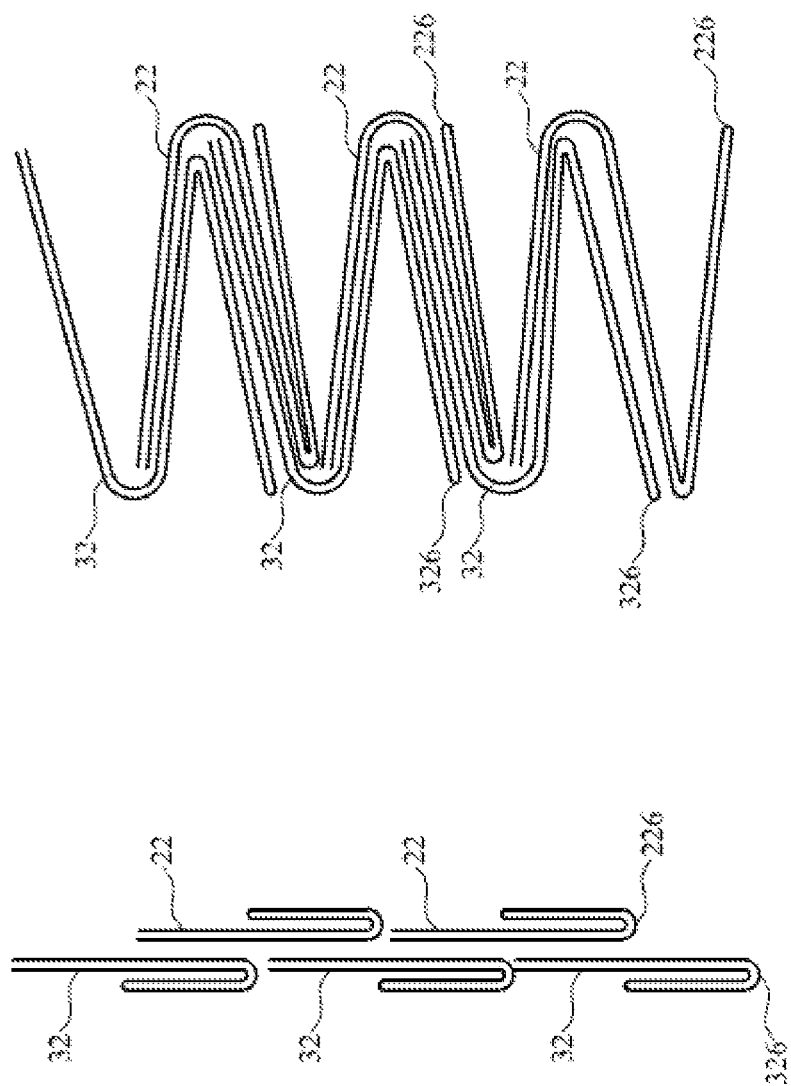

FOLDING MACHINE FOR FOLDING FIBER PRODUCTS AND STACK OF FIBER PRODUCTS PRODUCED THEREBY

REFERENCE TO RELATED APPLICATIONS

This non-provisional application claims priority claim under 35 U.S.C. § 119(a) on Taiwan Patent Application No. 108104303 filed Feb. 1, 2019 the entire contents of which are incorporated herein by reference.

FIELD OF THE INVENTION

The invention relates to a folding machine for folding fiber products and a stack of fiber products produced by the folding machine, more particularly, to a folding machine that folds the fiber products with two folding devices working together to increase the folding efficiency of fiber products with three folds.

BACKGROUND

FIG. 1 is a schematic diagram of a conventional fiber-product folding device. As shown in the figure, the conventional folding device 10 for cutting and folding a fiber product 12 includes a cutter wheel 11, a turning wheel 13, a differential wheel 15, a first folding wheel 171, and a second folding wheel 173.

The cutter wheel 11 and the turning wheel 13 are adjacent and rotate in opposite directions; for example, the cutter wheel 11 rotates counterclockwise while the turning wheel 13 rotates clockwise. The cutter wheel has a plurality of cutters 111 disposed thereon, and the turning wheel 13 has a plurality of indentations 131 disposed on its surface, wherein during the rotation of the cutter wheel 11 and the turning wheel 13, the cutter 111 coincides with the indentation 131 and punctures the fiber product 12 at the indentation 131 as shown in FIG. 2.

The differential wheel 15 is adjacent to the turning wheel 13 and the first folding wheel 171 and receives the cut fiber product 12 from the turning wheel 13 and then transports it to the first folding wheel 171 as shown in FIG. 3. The differential wheel 15 has a perimeter that is different in length from that of the first folding wheel 171, and thus when the cut fiber product 12 is being transported by the differential wheel 15 to the first folding wheel 171, overlapping of the fiber product 12 would occur due to the difference in the perimeters or the rotating speeds of the differential wheel 15 or the first folding wheel 171, wherein the difference in rotating speeds may be that the rotating speed of the differential wheel 15 is faster than that of the first folding wheel 171. Subsequently, the first folding wheel 171 and the second folding wheel 173 fold the partially-overlapped fiber product 12 to produce the interfolded fiber products 12 in twofolds shown in FIGS. 4 and 5 that we commonly see on the market.

SUMMARY

An object of the invention is to provide a folding machine for folding fiber products into three folds with improved folding efficiency. Conventionally, fiber products are folded by a single-sided folding device to produce fiber products with twofolds, and to enhance the folding efficiency, two folding devices are sometimes disposed at two sides respectively to fold the fiber products. However, the two aforementioned folding devices are only applicable for producing fiber products with twofolds, not for fiber products with three folds. Hence, a folding machine of the invention is modified to use two of the same folding machines disposed respectively at two sides that fold the fiber products at the same time and together to make fiber products into three folds, thereby effectively increasing the production efficiency for fiber products with three folds.

It is an object of the invention to provide a folding machine for folding fiber products, wherein a folding-line wheel and a platen wheel are disposed on a delivery wheel for folding fiber products carried on the delivery wheel for a first time, and then the once-folded fiber products are transported to a folding wheel to be folded for a second time, thereby forming a stack of fiber products with three folds.

Another object of the invention is to provide a folding machine for folding fiber products, wherein a plurality of folding-line wheels and a plurality of platen wheels are disposed on a delivery wheel for folding fiber products carried on the delivery wheel in half and then folding the half-folded fiber products for a first time. The once-folded fiber products are transported to a folding wheel to be folded for a second time, thereby forming a stack of double-layer fiber products with three folds.

To achieve the aforementioned objects, the invention provides a folding machine for folding fiber products, which includes a first folding device and a second folding device. The first folding device includes: a first cutting device for cutting a first fiber product; a first delivery wheel, which receives the cut first fiber product from the first cutting device; a first folding-line wheel adjacent to the first delivery wheel, wherein the first folding-line wheel and the first delivery wheel are used to make a first folding line on the first fiber product; a first platen wheel adjacent to the first delivery wheel and disposed downstream of the first folding-line wheel, wherein the first platen wheel and the first delivery wheel are used to fold the first fiber product along the first folding line; and a first folding wheel, which is adjacent to the first delivery wheel and receives therefrom the first fiber product. The second folding device includes: a second cutting device for cutting a second fiber product; a second delivery wheel, which receives the cut second fiber product from the second cutting device; a second folding-line wheel adjacent to the second delivery wheel, wherein the second folding-line wheel and the second delivery wheel are used to make a first folding line on the second fiber product; a second platen wheel adjacent to the second delivery wheel and disposed downstream of the second folding-line wheel, wherein the second platen wheel and the second delivery wheel are used to fold the second fiber product along the first folding line; and a second folding wheel, which is adjacent to the second delivery wheel and receives therefrom the second fiber product. The first folding wheel and the second folding wheel are used to make a second folding line on the first fiber product and the second fiber product that pass through between the two folding wheels and to fold the first fiber product and the second fiber product along the second folding line.

A stack of fiber products produced by a folding machine of the invention includes: a plurality of first fiber products and a plurality of second fiber products. Each of the first fiber products includes a front end, a back end, a first folding line, and a second folding line, wherein a distance between the first folding line and the front end is one third of the length of the first fiber product, and a distance between the second folding line and the back end is one third of the length of the first fiber product. The first fiber product is folded along the first folding line and the second folding line, wherein a first fold section is formed from the folding of the first folding line. Each of the second fiber product includes a front end, a back end, a first folding line, and a second folding line, wherein a distance between the first folding line and the front end is one third of the length of the second fiber product, and a distance between the second folding line and the back end is one third of the length of the second fiber product. The second fiber product is folded along the first folding line and the second folding line, wherein a first fold section is formed from the folding of the first folding line. The first fiber product and the second fiber product are alternately arranged, wherein the first fold section of the first fiber product is covered by the second fiber product adjacent thereto, and the first fold section of the second fiber product is covered by the first fiber product adjacent thereto.

The folding machine as described above, wherein the perimeter of the first delivery wheel is greater than the perimeter of the first folding wheel, and the perimeter of the second delivery wheel is greater than the perimeter of the second folding wheel.

The folding machine as described above, wherein the perimeter of the first folding wheel is two thirds of the perimeter of the first delivery wheel, and the perimeter of the second folding wheel is two thirds of the perimeter of the second delivery wheel.

The folding machine as described above, wherein each of the first fiber product and the second fiber product includes a front end and a back end, and a direction going from the back end towards the front end is a transport direction of the first fiber product and the second fiber product. The first delivery wheel and the first folding-line wheel make the first folding line at one third of the length of the first fiber product distant from the front end, and the second delivery wheel and the second folding-line wheel make the first folding line at one third of the length of the second fiber product distant from the front end.

The folding machine as described above, wherein the second folding line is formed by the first folding wheel and the second folding wheel and located at one third of the length of the first fiber product/the second fiber product distant from the back end.

The folding machine as described above, wherein each of the first delivery wheel and the second delivery wheel includes at least one indention and at least one adhesive hole, and each of the first folding-line wheel and the second folding-line wheel includes at least one protrusion and at least one adhesive hole. The protrusions of the first folding-line wheel and the second folding-line wheel respectively conform to the indentations of the first delivery wheel and the second delivery wheel, and are respectively used to make the first folding lines on the first fiber product carried on the first deliver wheel and on the second fiber product carried on the second delivery wheel.

The folding machine as described above, wherein each of the first folding wheel and the second folding wheel includes at least one protrusion and at least one indentation, and the protrusion and the indentation of the first folding wheel conform to the indentation and the protrusion of the second folding wheel, respectively, to make the second folding lines on the first fiber product and the second fiber product.

The folding machine as described above, wherein the first cutting device includes a first cutting knife and a first cutter wheel adjacent thereto and cuts the first fiber product that passes through between the two, and the second cutting device includes a second cutting knife and a second cutter wheel and cuts the second fiber product that passes through between the two.

The folding machine as described above, further includes at least one third folding-line wheel, at least one third platen wheel, at least one fourth folding-line wheel, and at least one fourth platen wheel, wherein the third folding-line wheel and the third platen wheel are disposed between the first cutting device and the first folding-line wheel and are used to fold the first fiber product in half, and the fourth folding-line wheel and the fourth platen wheel are disposed between the second cutting device and the second folding-line wheel and are used to fold the second fiber product in half.

BRIEF DESCRIPTION OF THE DRAWINGS

The structure as well as preferred modes of use, further objects, and advantages of this invention will be best understood by referring to the following detailed description of some illustrative embodiments in conjunction with the accompanying drawings, in which:

FIGS. 13 and 14 are schematic diagrams of fiber products folded and stacked by a folding machine according to an embodiment of the invention.

FIGS. 16 and 17 are schematic diagrams of fiber products folded and stacked by a folding machine according to another embodiment of the invention.

DETAILED DESCRIPTION OF THE PREFERRED EMBODIMENTS

Figure 6:
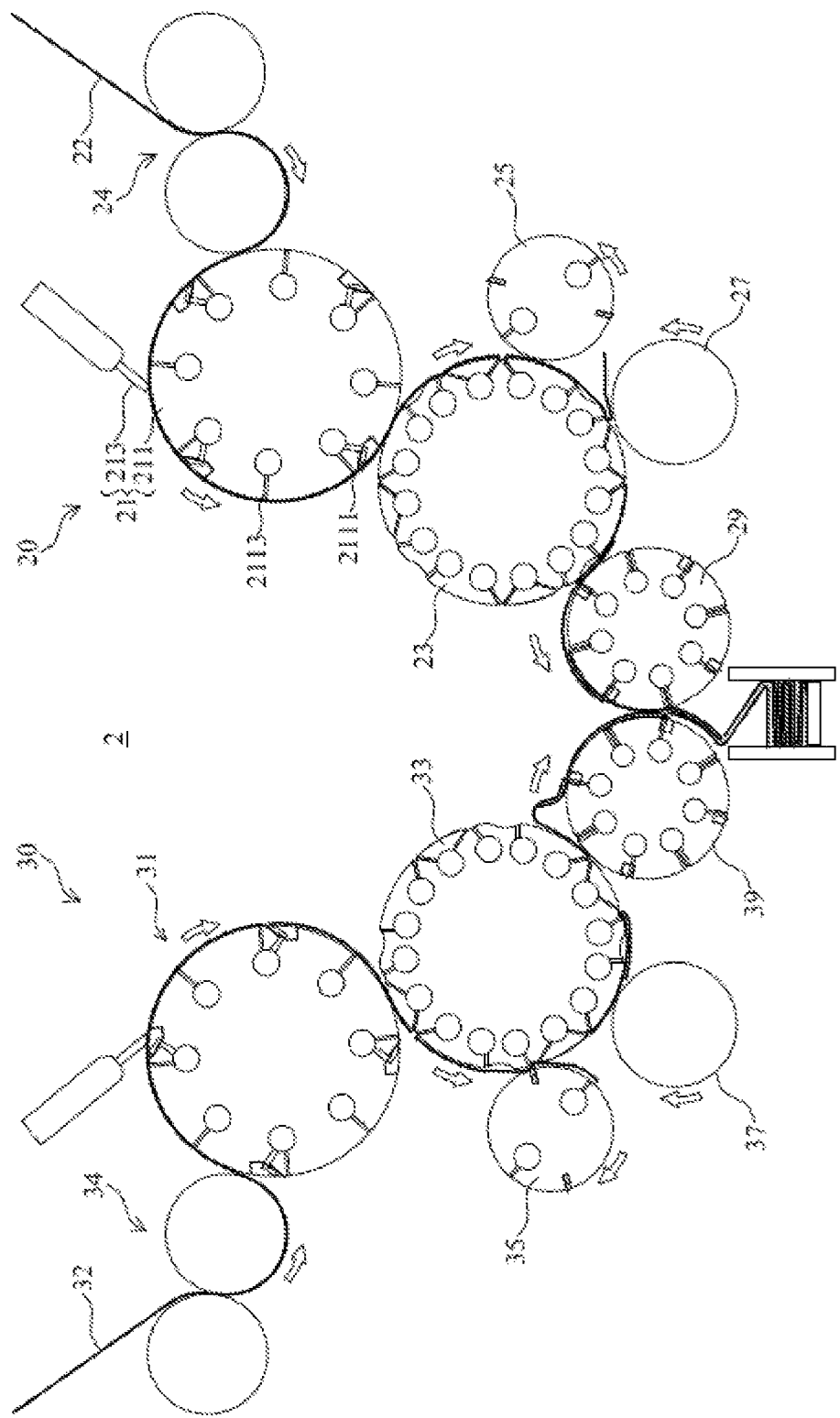
FIG. 6 is a schematic diagram of a folding machine for folding fiber products according to an embodiment of the invention.

FIG. 6 is a schematic diagram of a folding machine for folding fiber products according to a preferred embodiment of the invention. The folding machine 2 is capable of folding a fiber product 22/32, such as toilet paper, tissue paper, or paper towel, into three folds, and includes a first folding device 20 and a second folding device 30. The first folding device 20 and the second folding device 30 are used to make two folding lines on the folding product 22/32 and to fold the fiber product 22/32 along the two folding lines.

The first folding device 20 includes a first cutting device 21, a first delivery wheel 23, a first folding-line wheel 25, a first platen wheel 27, and a first folding wheel 29, wherein the first cutting device 21 cuts the first fiber product 22 after receiving it from a first transport wheel set 24.

In one embodiment of the invention, the first cutting device 21 includes a first cutter wheel 211 and a first cutting knife 213, wherein the first cutter wheel includes at least one cutter 2111. When the first cutter wheel 211 rotates relative to the first cutting knife 213, the cutter 2111 on the first cutter wheel 211 comes in contact with the first cutting knife 213 and cuts the first fiber product 22 passing through and between the cutter 2111 and the first cutting knife 213, and the first fiber product 22 with fixed length is formed thereby.

Specifically, the first cutter wheel 211 further includes at least one adhesive hole 2113 in which negative pressure can be generated, and thus the first fiber product 22 transported by the first transport wheel set 24 is adhered to the surface of the first cutter wheel 211, making it easier for the first cutter wheel 211 and the first cutting knife 213 to cut the first fiber product 22.

The first delivery wheel 23 is disposed downstream of the first cutting device 21 and receives the cut first fiber product 22 from the first cutting device 21. In one embodiment of the invention, the first delivery wheel 23 and the first cutter wheel 211 are adjacent and the first cutter wheel 211 receives the first fiber product 22.

Figure 7:
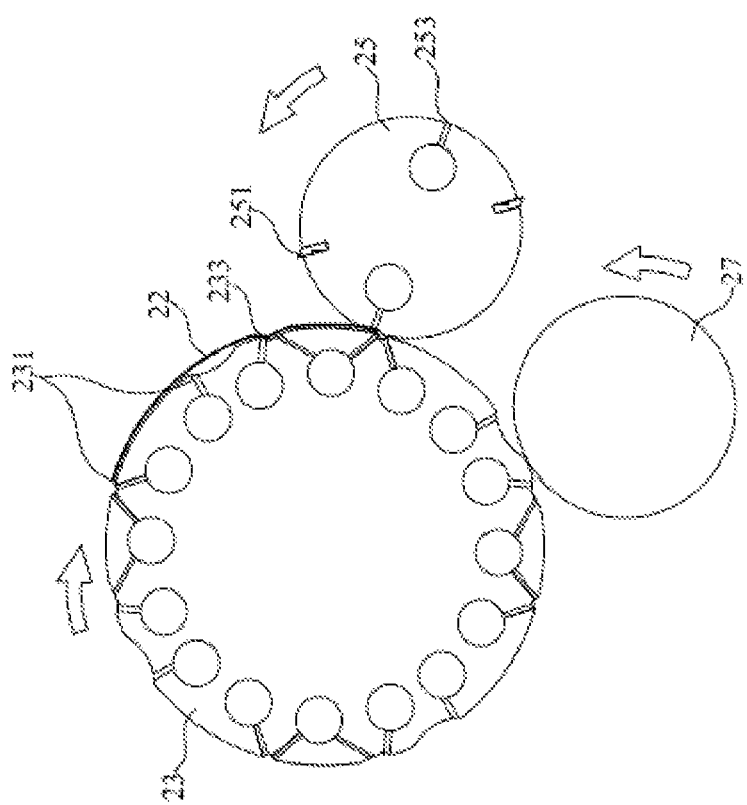

The first delivery wheel 23 includes at least one adhesive hole 231 in which negative pressure can be generated such that the first fiber product 22 carried on the first cutter wheel 211 is adhered to the surface of the first delivery wheel 23, as shown in FIG. 7. In specific, when the adhesive hole 231 of the first delivery wheel 23 faces the adhesive hole 2113 of the first cutter wheel 211, negative pressure is generated in the adhesive hole 231 of the first delivery wheel 23 but not in the adhesive hole 2113 of the first cutter wheel 211, so that the first fiber product 22 is adhered by the adhesive hole 231 of the first delivery wheel 23.

Figure 8:
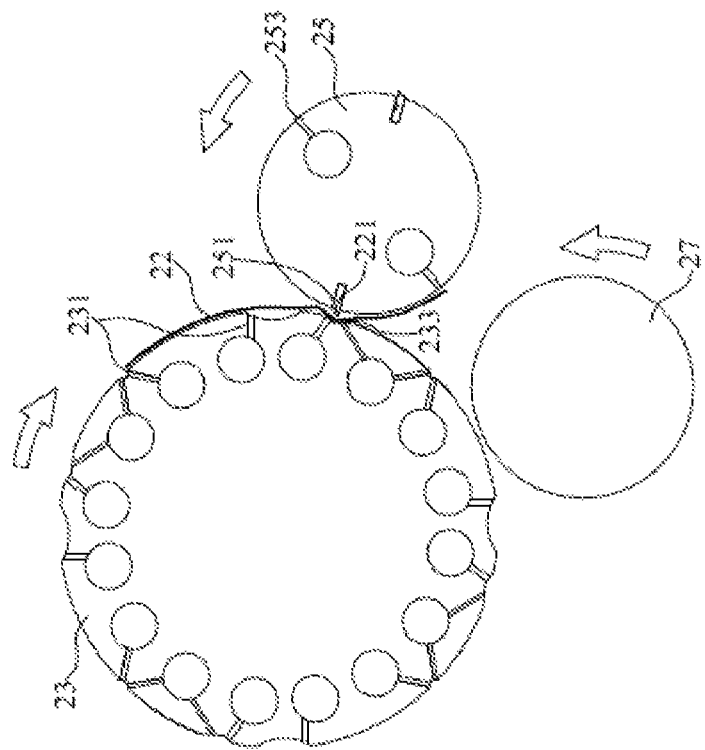
FIGS. 7-12 are enlarged views of some components of a folding machine for folding fiber products according to an embodiment of the invention.

The first folding-line wheel 25 and the first delivery wheel 23 are adjacent, and are used to make a first folding line 221 on the first fiber product 22 passing through the two wheels 25, 23 as shown in FIGS. 8, 13, and 14. The first delivery wheel 23 includes at least one indentation 233 and at least one adhesive hole 231 and the first folding-line wheel includes at least one protrusion 251 and at least one adhesive hole 253.

More specifically, when the first delivery wheel 23 and the first folding-line wheel 25 rotate in different directions, like the first delivery wheel 23 rotates clockwise and the first folding-line wheel rotates counterclockwise, the adhesive hole 253 of the first folding-line wheel faces the adhesive hole 231 of the first delivery wheel 23. At this time negative pressure is generated in the adhesive hole 253 of the first folding-line wheel 25 and the generation of negative pressure in the corresponding adhesive hole 231 of the first delivery wheel 23 is stopped, so that one end of the first fiber product 22 is adhered by the adhesive hole 253 of the first folding-line wheel 25 as shown in FIG. 7.

The first folding-line wheel 25 and the first delivery wheel 23 continue to rotate, wherein a portion of the first fiber product 22 attaches to the surface of the first folding-line wheel 25. Then the protrusion 251 of the first folding-line wheel 25 meets the indentation 233 of the first delivery wheel 23 and, on the first fiber product 22 between the two, makes the first folding line 221 as shown in FIG. 8.

Figure 9:
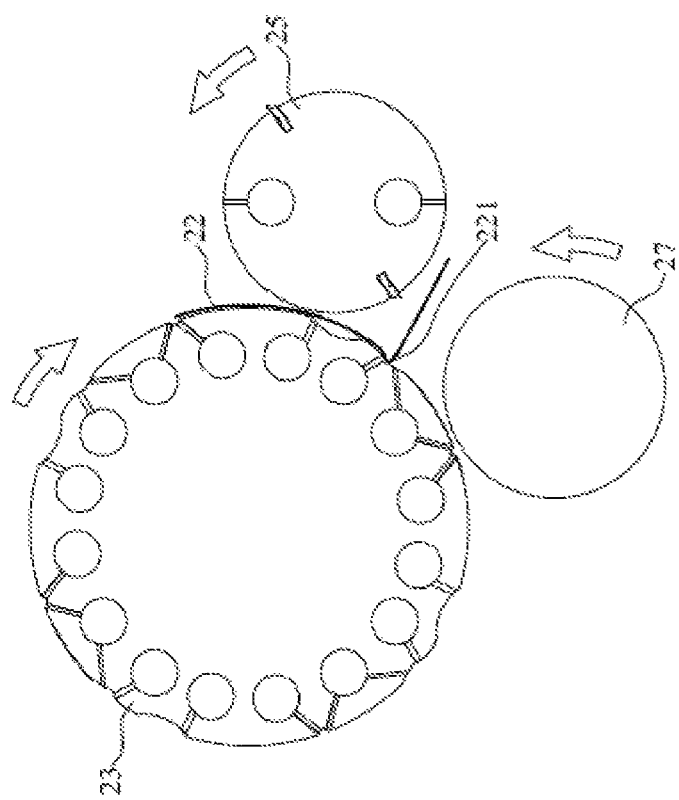

After the first folding line 221 has been formed, the generation of negative pressure in the adhesive hole 253 of the first folding-line wheel 25 stopped and the adhered first fiber product 22 is released. At the same time, the first delivery wheel 23 continues to transport the first fiber product 22, wherein the first fiber product 22 forms a pre-fold status along the first folding line 221 as shown in FIG. 9.

Figure 10:
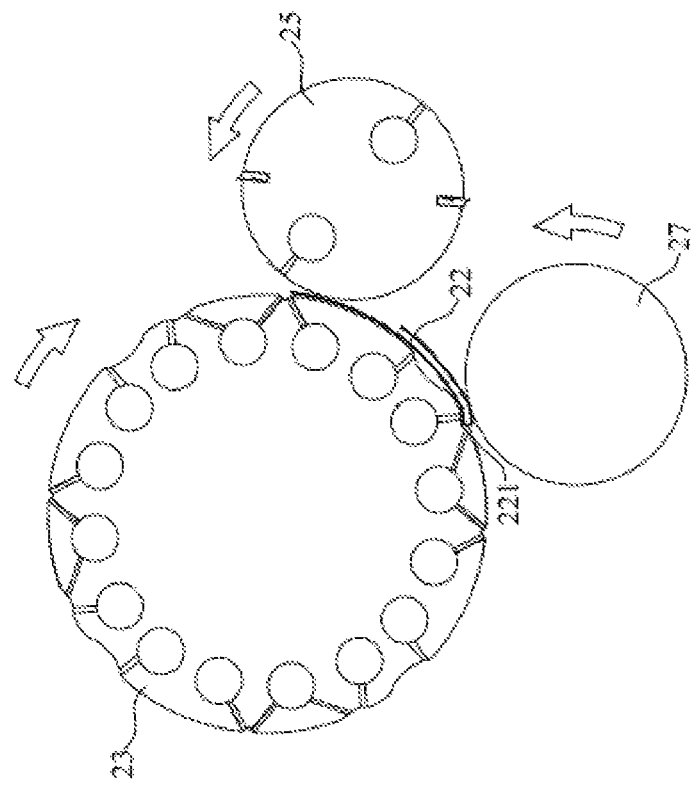

The first platen wheel 27 is disposed downstream of the first folding-line wheel 25 and adjacent to the first delivery wheel 23, wherein the first platen wheel 27 can be a smooth-surfaced circular column. With continuing rotation of the first delivery wheel 23, the first fiber product 22 in the pre-fold status is transported to the first platen wheel 27. The first platen wheel 27 and the first delivery wheel 23 press the passing-through first fiber product 22 along the first folding line 221, thereby folding the first fiber product 22 for a first time along the first folding line 221 as shown in FIG. 10.

More particularly, referring to FIGS. 13 and 14, two ends of the first fiber product 22 can be defined as a front end 225 and a back end 227, respectively, according to a transport direction of the first fiber product 22, wherein a direction going from the back end 227 towards the front end 225 is the transport direction. A distance between the first folding line 221 formed on the first fiber product 22 and the front end 225 is about one third of the length of the first fiber product 22, and a first fold section 224 is formed after the first fiber product 22 is folded along the first folding line 221.

The first folding wheel 29 is adjacent to the first delivery wheel 23 and receives threrefrom the once-folded first fiber product 22, wherein the length of the first fiber product 22 that has been folded for a first time is smaller than the length of an unfolded first fiber product 22. In other words, the length of the first fiber product 22 received by the first delivery wheel 23 from the first cutting device 21 is greater than the length of the first fiber product 22 received by the folding wheel 23 from the first delivery wheel 23, and therefore the perimeter of the first folding wheel 29 is smaller than the perimeter of the first delivery wheel 23.

Figure 11:
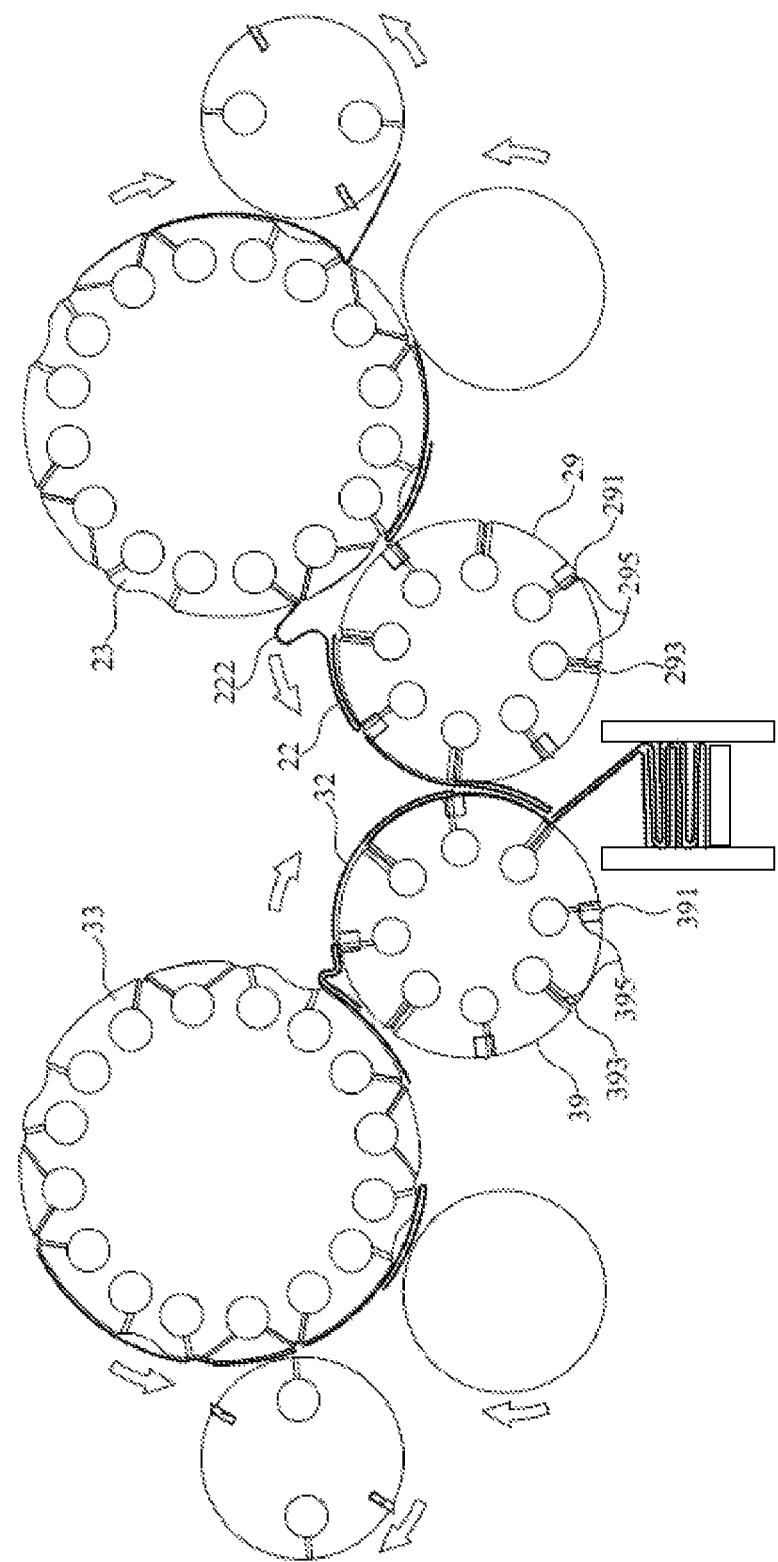
Figure 12:
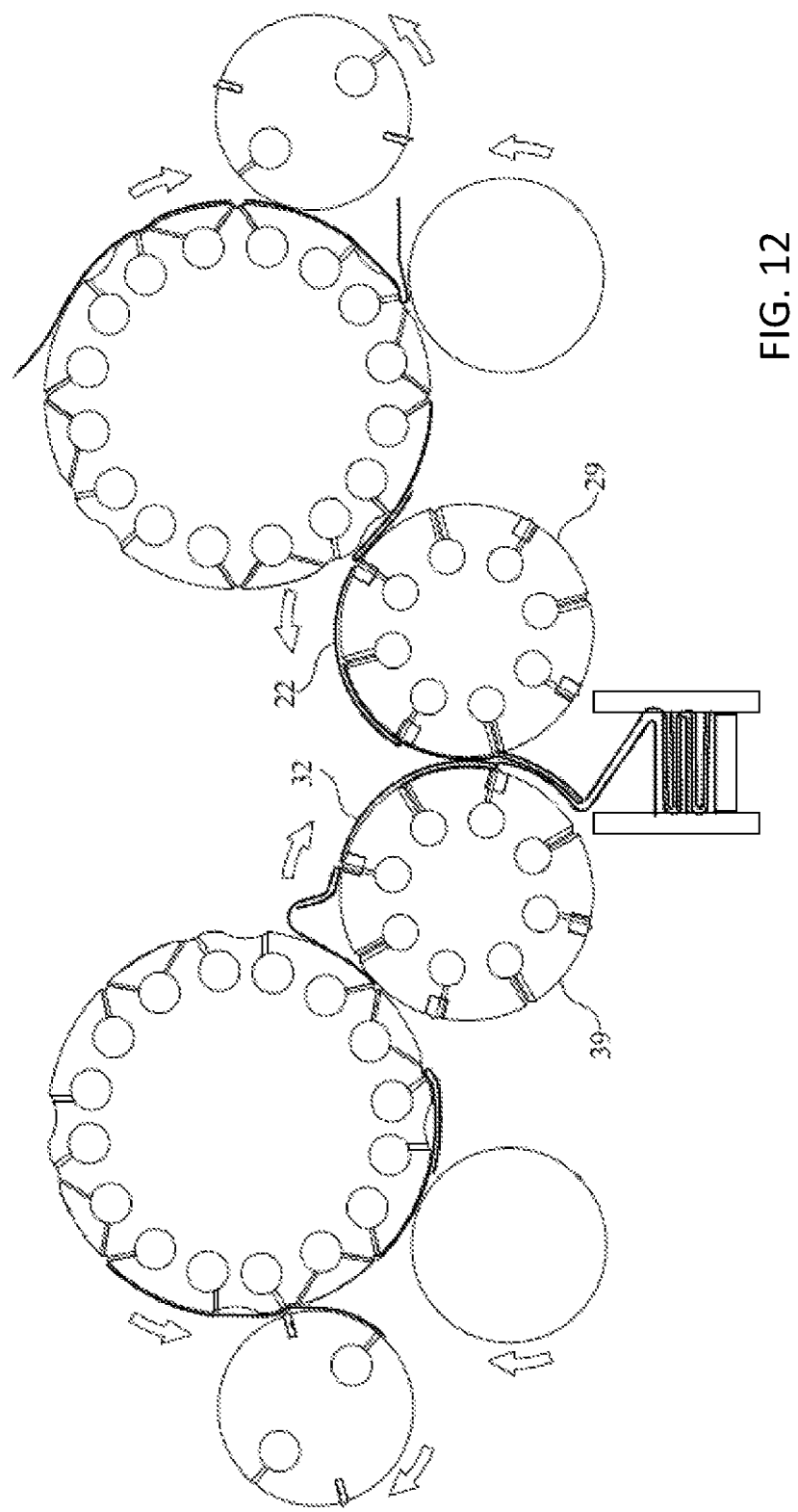

Referring to FIGS. 11 and 12, the first folding wheel 29 includes at least one protrusion 291, at least one indentation 293, and at least one adhesive hole 295, wherein the protrusion 291 and the indentation 293 are disposed on the surface of the first folding wheel 29 in an alternate arrangement, and the adhesive hole 295 is disposed inside or near the protrusion 291 and the indentation 293, so that the first fiber product 22 is adhered to the protrusion 291 and/or the indentation 293.

In one embodiment of the invention, when the folding machine 2 produces the fiber product 22 with three folds, the first folding-line wheel 25 and the first delivery wheel 23 make the first folding line 221 that is about one third of the length of the first fiber product 22 distant from the front end 225 of the first fiber product 22, and the first platen wheel 27 and the first delivery wheel 23 fold the first fiber product 22 for a first time along the first folding line 221 at about one third of the first fiber product 22.

The length of the first fiber product 22 that has been folded for a first time is about two thirds of its original length, and the perimeter of the first folding wheel 29 is two thirds of the perimeter of the first delivery wheel 23, thus the unfolded first fiber product 22 is adhered smoothly to the surface of the first delivery wheel 23 and the once-folded first fiber product 22 is also adhered smoothly to the surface of the first folding wheel 29.

During the transportation of the once-folded first fiber product 22 to the first folding wheel 29 by the first delivery wheel 23, one end of the first fiber product 22 is adhered to the first folding wheel 29 and the first fiber product 22 is rotated thereby, whilst the other end of the first fiber product 22 is still adhered to the first delivery wheel 23.

Since the perimeter of the first delivery wheel 23 is greater than that of the first folding wheel 29, when the once-folded first fiber product 22 is transported to the first folding wheel 29 by the first delivery wheel 23, a part of the first fiber product 22 between the first delivery wheel 23 and the first folding wheel 29 forms a distortion part 222 as shown in FIGS. 11 and 12.

Figure 1:
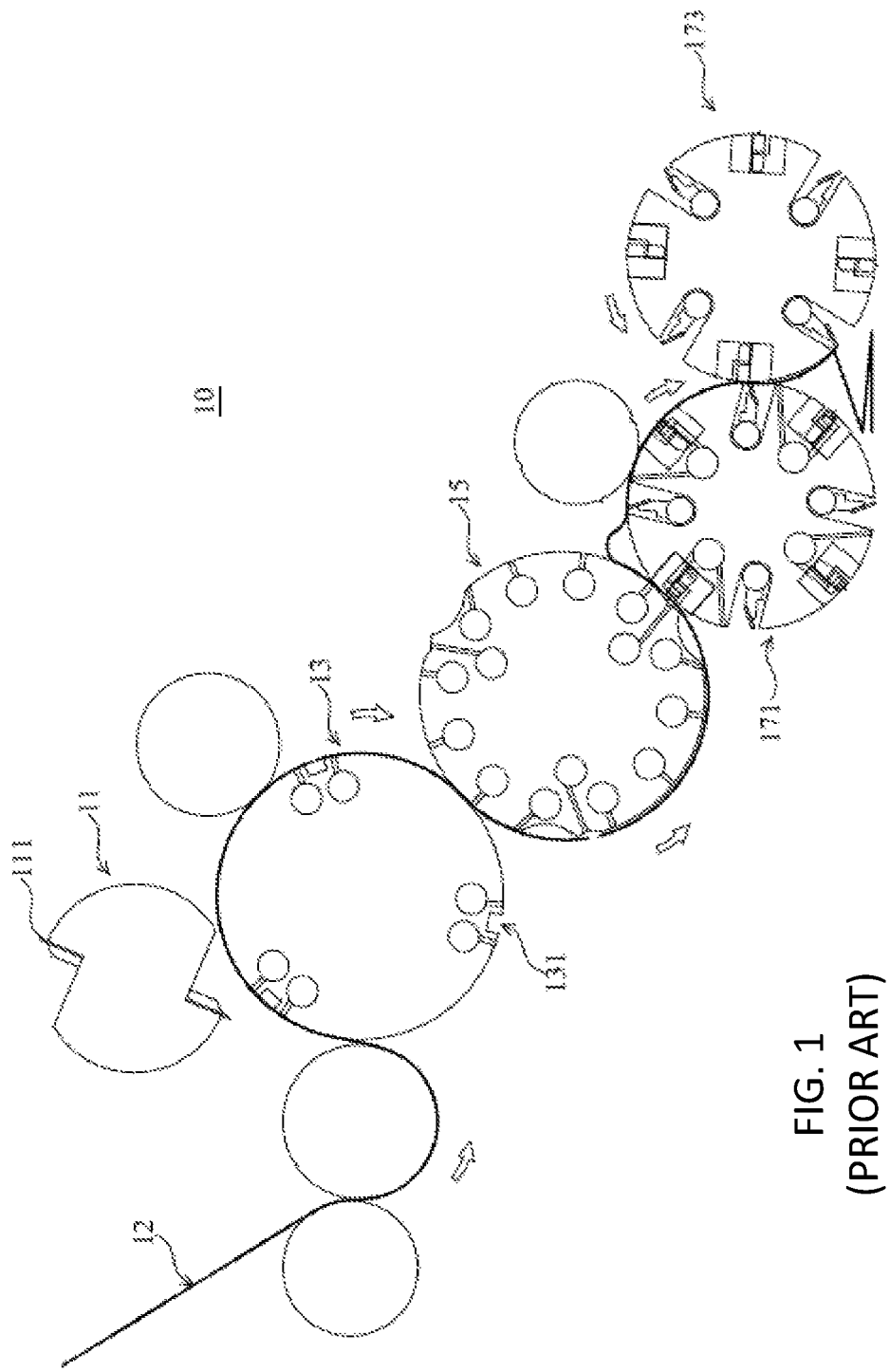
FIG. 1 is a schematic diagram of a conventional fiber-product folding device.
Figure 2:
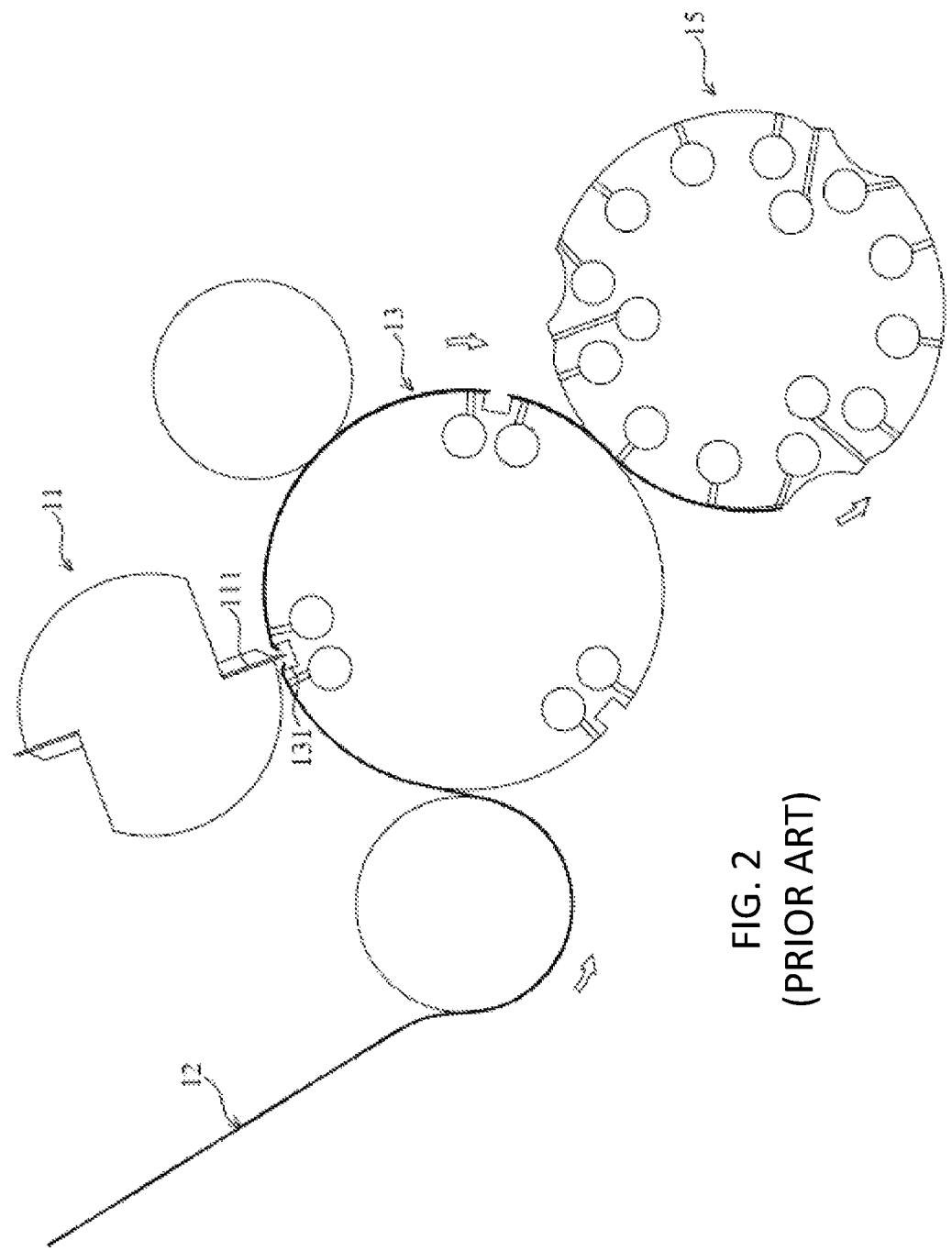
FIGS. 2 and 3 are enlarged views of some components of a conventional fiber-product folding device.
Figure 3:
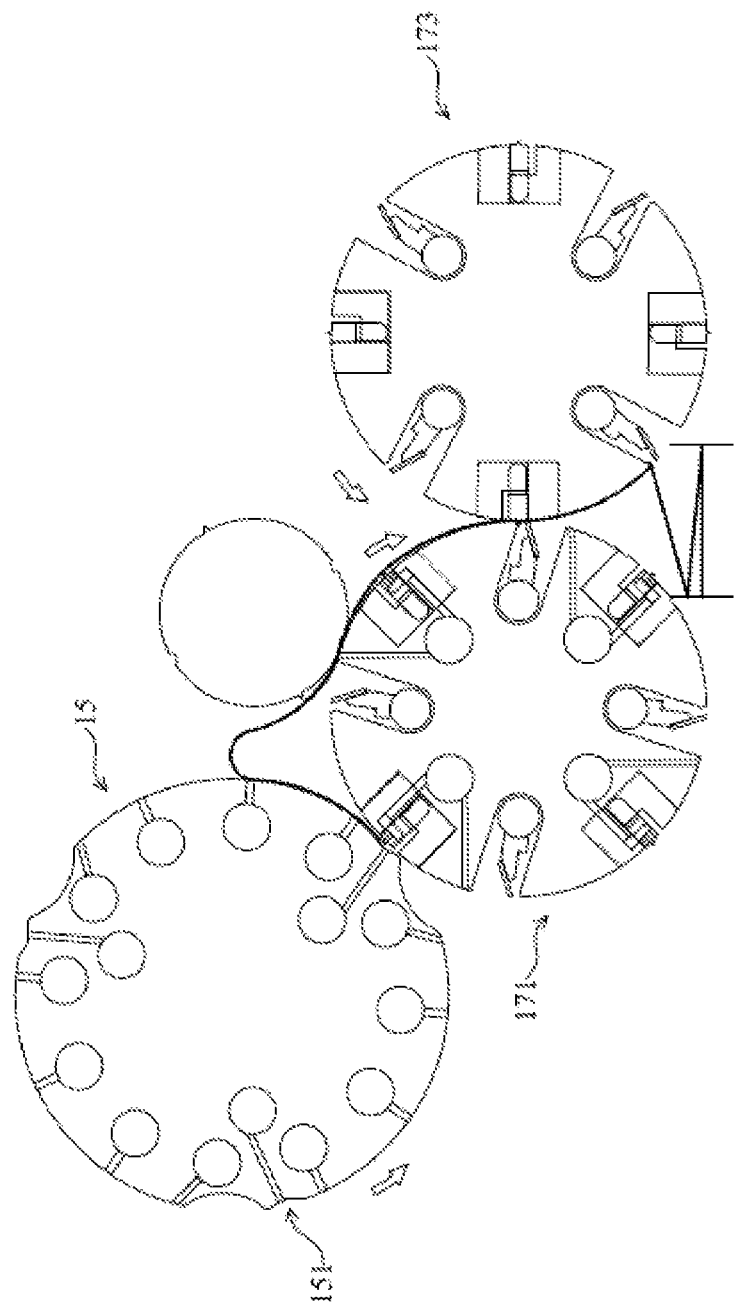
Figure 5:
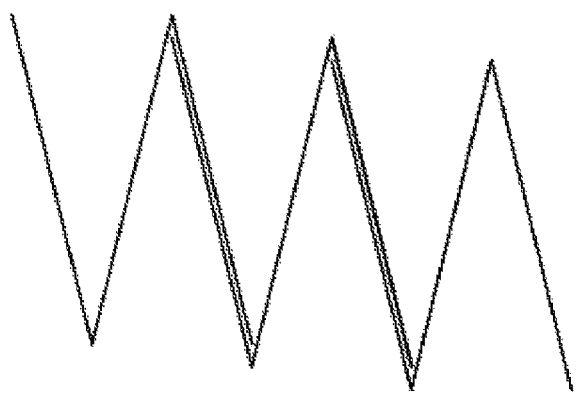
FIGS. 4 and 5 are schematic diagrams of fiber products folded and stacked by a conventional fiber-product folding device.
Figure 4:
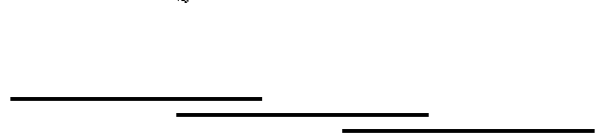

It is to be noted that although the distortion part 222 formed during the transportation of the first fiber product 22 between the first delivery wheel 23 and the first folding wheel 29 of the invention seems similar to the prior art in FIG. 1, the distortion part 222 of the invention does not cover over a next first fiber product 22 when the first delivery wheel 23 releases the first fiber product 22, and hence the adjacent first fiber product 22 on the first folding wheel 29 does not overlap each other.

The second folding device 30 includes a second cutting device 31, a second delivery wheel 33, a second folding-line wheel 35, a second platen wheel 37, and a second folding wheel 39, wherein the second cutting device 31 receives the second fiber product 32 from a second transport wheel set 34 and cuts the second fiber product 32.

The second delivery wheel 33 receives the cut second fiber product 32 from the second cutting device 31 and makes, with the second folding-line wheel 35, a first folding line 321 on the second fiber product 32. The second delivery wheel 33 and the second platen wheel 37 fold the second fiber product 32 for a first time along the first folding line 321 and transport the once-folded second fiber product 32 to the second folding wheel 39. The configuration and operation of the second folding device 30 is similar to that of the first folding device 20, and therefore will not be repeated again herein.

In addition, although the configuration of the second folding device 30 is similar to that of the first folding device 20, their operations are not in synchronization. In particular, the rotating speeds of the first folding wheel 29 and the second folding wheel 39 are the same, but there is a phase difference between the two folding wheels 29, 39 so as to fold the first fiber product 22 and the second fiber product 32 for a second time.

Referring to FIGS. 13 and 14, two ends of the second fiber product 32 are respectively defined to be a front end 325 and a back end 327 according to a transport direction of the second fiber product 22, wherein a direction going from the back end 327 towards the front end 325 is the transport direction. The first folding line 321 formed on the second fiber product 32 is about one third of the length of the second fiber product 32 distant from the front end 325, and the second fiber product 32 forms a first fold section 324 after being folded along the first folding line 321.

The once-folded first fiber product 22 and the once-folded fiber product 32 are sequentially transported to the first folding wheel 29 and the second folding wheel 39, wherein the first folding wheel 29 and the second folding wheel 39 are adjacent and fold the first fiber product 22 and the second fiber product 32, which pass through between the two folding wheels 29, 39, for a second time.

The second folding wheel 39 includes at least one protrusion 391, at least one indentation 393, and at least one adhesive hole 395, wherein the protrusion 391 and the indentation 393 are disposed on the surface of the second folding wheel 39 in an alternate arrangement. The adhesive hole 395 is disposed inside or near the protrusion 391 and the indentation 393, so that the second fiber product 32 is adhered to the protrusion 391 and/or the indentation 393.

The first folding wheel 29 and the second folding wheel 39 are used to make a second folding line 223/323 on the first fiber product 22 and/or the second fiber product 32, wherein the second folding line 223/323 is at about where the front end 225/325 overlaps the fiber product 22/32. Then the first fiber product 22 and/or the second fiber product 32 is folded for a second time along the second folding line 223/323, thereby forming a fiber product with three folds.

The protrusion 291 and the indentation 293 of the first folding wheel 29 conform to the indentation 393 and the protrusion 391 of the second folding wheel 39, respectively. When the once-folded first fiber product 22 is transported by the first folding wheel 29 to and in between the first and second folding wheels 29, 39, the protrusion 391 of the second folding wheel 39 meets the indentation 293 of the first folding wheel 29, making the second folding line 223 on the first fiber product 22 between the two folding wheels 29, 39, and subsequently folding the first fiber product 22 for a second time along the second folding line 223. Moreover, the second fiber product 32 transported by the second folding wheel 39 overlaps the first fold section 224 of the first fiber product 22 transported by the first folding wheel 29, as shown in FIG. 11.

It is evident that the first fiber product 22 transported by the first folding wheel 29 also overlaps the first fold section 324 of the second folding product 32 transported by the second folding wheel 39, as shown in FIG. 12, and so the first fiber product 22 and the second fiber product 32 adjacent to each other are alternately stacked to form interfold tissue paper with three folds.

FIGS. 13 and 14 are schematic diagrams illustrating a stack of fiber products produced and stacked by the folding machine according to an embodiment of the invention. As shown in the figures, the stacked of fiber products includes a plurality of first fiber products 22 and a plurality of second fiber products 32, and the adjacent first and second fiber products 22 and 32 are overlapped in partial regions and thus form the interfold tissue paper.

The first fiber product 22 includes a front end 225, a back end 227, a first folding line 221, a second folding line 223, and a first fold section 224, wherein a direction going from the back end 227 towards the front end 225 is the transport direction of the first fiber product 22. The distance between the first folding line 221 and the front end 225 is about one third of the length of the first fiber product 22, wherein the first fiber product 22 is folded along the first folding line 221 and forms the first fold section 224. The distance between the second folding line 223 and the back end 227 is about one third of the length of the first fiber product 22, wherein the second folding line 223 and the front end 225 overlap in location.

The second fiber product 32 includes a front end 325, a back end 327, a first folding line 321, a second folding line 323, and a first fold section 324, wherein a direction going from the back end 327 towards the front end 325 is the transport direction of the second fiber product 32. The distance between the first folding line 321 and the front end 325 is about one third of the length of the second fiber product 32, wherein the second fiber product 32 is folded along the first folding line 321 and forms the first fold section 324. The distance between the second folding line 323 and the back end 327 is about one third of the length of the second fiber product 32, wherein the second folding line 323 and the front end 325 overlap in location.

The first fiber product 22 and the second fiber product 32 are alternately arranged and stacked, wherein the first fold section 224 of the folded first fiber product 22 is covered by the second fiber product 32 adjacent thereto, for example, covered by a region between the back end 327 and the second folding line 323 of the second fiber product 32, and the first fold section 324 of the second fiber product 32 is covered by the first fiber product 22 adjacent thereto, for example, covered by a region between the back end 227 and the second folding line 223 of the first fiber product 22.

Moreover, the region of the first fiber product 22 between its back end 227 and its second folding line 223 is covered by a region of a previous first fiber product 22 between its front end 225 and its first folding line 221, wherein the region of the first fiber product 22 between its back end 227 and its second folding line 223 is located between the second fiber product 32 and the previous first fiber product 22, and the region of the second fiber product 32 between its back end 327 and its second folding line 323 is located between the first fiber product 22 and a previous second fiber product 32.

For the convenience of description, the fiber products are divided into first fiber products 22 and second fiber products 32, but in practical application, the first fiber products 22 and the second fiber products 32 can be the same material and has the same size and thickness.

Figure 15:
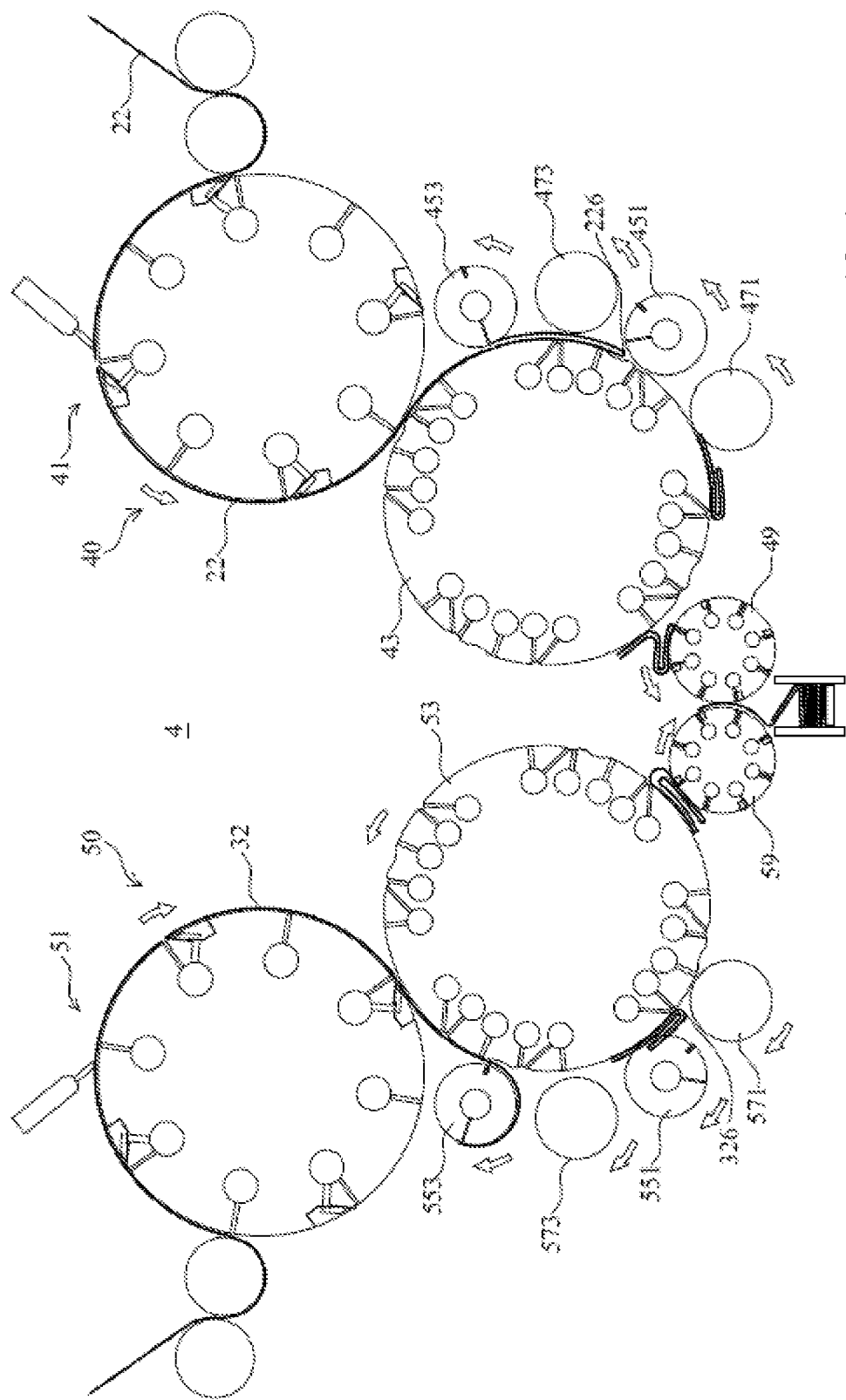
FIG. 15 is a schematic diagram of a folding machine for folding fiber products according to another embodiment of the invention.

FIG. 15 is a schematic diagram illustrating a folding machine for folding fiber products according to another embodiment of the invention. In the figure, the folding machine 4 includes a first folding device 40 and a second folding device 50 for folding the fiber products 22/32 passing through and between the two folding devices 40, 50.

The first folding device 40 includes a first cutting device 41, a first delivery wheel 43, a first folding-line wheel 451, a first platen wheel 471, a third folding-line wheel 453, a third platen wheel 473, and a first folding wheel 49. The second folding device 50 includes a second cutting device 51, a second delivery wheel 53, a second folding-line wheel 551, a second platen wheel 571, a fourth folding-line wheel 553, a fourth platen wheel 573, and a second folding wheel 59.

The folding machine 4 described in this embodiment is similar to the folding machine 2 described in previous embodiment and differs in that the folding machine 4 further includes the third folding-line wheel 453, the third platen wheel 473, the fourth folding-line wheel 553, and the fourth platen wheel 573. The third folding-line wheel 453 and the third platen wheel 473 are adjacent to the first devilry wheel 43 and disposed between the first folding-line wheel 451 and the first cutting device 41. The fourth folding-line wheel 553 and the fourth platen wheel 573 are adjacent to the second delivery wheel 53 and disposed between the second folding-line wheel 551 and the second cutting device 51.

The first folding device 40 cuts the received first fiber products 22 with the first cutting device 41 and thus first fiber products 22 with fixed length are formed. The first delivery wheel 43 receives the cut first fiber product 22 from the first cutting device 41, and the third folding-line wheel 453 makes a center folding line 226 on the center line or the bisecting line of the first fiber product 22 carried by the first delivery wheel 43.

The third platen wheel 473 is disposed downstream of the third folding-line wheel 453, wherein the third platen wheel 473 and the first delivery wheel 43 press the first fiber product 22 passing therethrough along the center folding line 226 to fold the first fiber product 22 in half along the center folding line 226.

The first fiber product 22 that has been folded in half is transported to the first folding-line wheel 451 and the first platen wheel 471 to be folded again at one third of its length. The first folding wheel 451 and the first platen wheel 471 of this embodiment fold the first fiber product 22 in a similar way to that of the first folding wheel 25 and the first platen wheel 27 in the previous embodiment, and the difference is that the first fiber product 22 being folded by the first folding wheel 451 and the first platen wheel 471 in this embodiment had been folded in half.

The configuration and operation of the second folding device 50 is similar to that of the first folding device 40, wherein the fourth folding-line wheel 553 makes a center folding line 326 on a center line or a bisecting line of the second fiber product 32 carried by the second delivery wheel 53. The fourth platen wheel 573 and the second delivery wheel 53 fold the second fiber product 32 in half along the center folding line 326, and then the second folding-line wheel 551 and the second platen wheel 571 fold the second fiber product 32 that has been folded in half at one third of its length.

The first folding wheel 49 and the second folding wheel 59 also operate similarly to the first folding wheel 29 and the second folding wheel 39 in the previous embodiment and hence will not be repeated herein.

Furthermore, in the folding machine 2, the perimeter of the first folding wheel 29 can be two thirds of the perimeter of the first delivery wheel 23, and the perimeter of the second folding wheel 39 is two thirds of the perimeter of the second delivery wheel 33. However, for the folding machine 4 of this embodiment, the perimeter of the first folding wheel 49 can be one third of the perimeter of the first delivery wheel 43, and the perimeter of the second folding wheel 59 is one third of the perimeter of the second delivery wheel 53.

The fiber products folded and stacked by the folding machine 4 of this embodiment are substantially the same as those folded and stacked by the folding machine 2 in the previous embodiment. As shown in FIGS. 16 and 17, the difference is that the first fiber product 22 and the second fiber product 32 produced by the folding machine 4 of this embodiment have a double-layer structure from being folded in half and are thicker in thickness.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

What is claimed is:

1. A folding machine for folding fiber products, comprising:
   a first folding device comprising:
      a first cutting device for cutting a first fiber product;
      a first delivery wheel, the first delivery wheel receiving the cut first fiber product from the first cutting device;
      a first folding-line wheel adjacent to the first delivery wheel, wherein the first folding-line wheel and the first delivery wheel make a first folding line on the first fiber product;
      a first platen wheel adjacent to the first delivery wheel and downstream of the first folding-line wheel, wherein the first platen wheel and the first delivery wheel fold the first fiber product along the first folding line; and
      a first folding wheel adjacent to the first delivery wheel, the first folding wheel receiving the first fiber product from the first delivery wheel; and
   a second folding device comprising:
      a second cutting device for cutting a second fiber product;
      a second delivery wheel, the second delivery wheel receiving the cut second fiber product from the second cutting device;
      a second folding-line wheel adjacent to the second delivery wheel, wherein the second folding-line wheel and the second delivery wheel make a first folding line on the second fiber product;
      a second platen wheel adjacent to the second delivery wheel and downstream of the second folding-line wheel, wherein the second platen wheel and the second delivery wheel fold the second fiber product along the first folding line; and a second folding wheel adjacent to the second delivery wheel, the second folding wheel receiving the second fiber product from the second delivery wheel, wherein the first folding wheel and the second folding wheel are adjacent and make a second folding line on the first fiber product and the second fiber product passing therethrough and fold the first fiber product and the second fiber product along the second folding line, wherein each of the first delivery wheel and the second delivery wheel includes at least one indentation and at least one adhesive hole, each of the first folding-line wheel and the second-folding line wheel includes at least one protrusion and at last one adhesive hole, and the protrusions of the first folding-line wheel and the second folding-line wheel conform, respectively, to the indentations of the first delivery wheel and the second delivery wheel to make the first folding lines, respectively, on the first fiber product carried by the first delivery wheel and on the second fiber product carried by the second delivery wheel, and wherein each of the first folding wheel and the second folding wheel includes at least one protrusion and at least one indentation, and the protrusion and the indentation of the first folding wheel conform respectively to the indentation and the protrusion of the second folding wheel to make the second folding line on the first fiber product and the second fiber product.

2. The folding machine of claim 1, wherein a perimeter of the first delivery wheel is greater than a perimeter of the first folding wheel, and a perimeter of the second delivery wheel is greater than a perimeter of the second folding wheel.

3. The folding machine of claim 2, wherein the perimeter of the first folding wheel is two thirds of the perimeter of the first delivery wheel, and the perimeter of the second folding wheel is two thirds of the perimeter of the second delivery wheel.

4. The folding machine of claim 3, wherein each of the first fiber product and the second fiber product comprises a front end and a back end, a direction going from the back end towards the front end is a delivery direction of the first fiber product and the second fiber product, the first delivery wheel and the first folding-line wheel make the first folding line on the first fiber product at one third of the length of the first fiber product distant from the front end, and the second delivery wheel and the second folding-line wheel make the first folding line on the second fiber product at one third of the length of the second fiber product distant from the front end.

5. The folding machine of claim 4, wherein the first folding wheel and the second folding wheel make the second folding line on the first fiber product and the second fiber product at one third of the length of the first fiber product and the second fiber product distant from the back end.

6. The folding machine of claim 1, wherein the first cutting device comprises a first cutting knife and a first cutter wheel, the first cutting knife and the first cutter wheel are adjacent and cut the first fiber product passing therethrough, and the second cutting device comprises a second cutting knife and a second cutter wheel, the second cutting knife and the second cutter wheel are adjacent and cut the second fiber product passing therethrough.

7. The folding machine of claim 1, further comprising at least one third folding-line wheel, at least one third platen wheel, at least one fourth folding-line wheel, and at least one fourth platen wheel, wherein the third folding-line wheel and the third platen wheel are disposed between the first cutting device and the first folding-line wheel for folding the first fiber product in half, and the fourth folding-line wheel and the fourth platen wheel are disposed between the second cutting device and the second folding-line wheel for folding the second fiber product in half.

8. A stack of fiber products produced by the folding machine of claim 1, comprising:

a plurality of first fiber products, each comprising a front end, a back end, a first folding line and a second folding line, the first fiber product being folded along the first folding line and the second folding line and forming a first fold section after being folded along the first folding line, wherein a distance between the first folding line and the front end is one third of the length of the first fiber product, and a distance between the second folding line and the back end is one third of the length of the first fiber product; and a plurality of second fiber products, each comprising a front end, a back end, a first folding line and a second folding line, the second fiber product being folded along the first folding line and the second folding line and forming a first fold section after being folded along the first folding line, wherein a distance between the first folding line and the front end is one third of the length of the second fiber product, and a distance between the second folding line and the back end is one third of the length of the second fiber product;

wherein the first fiber product and the second fiber product are alternately arranged, the first fold section of the first fiber product is covered by the second fiber product adjacent thereto, and the first fold section of the second fiber product is covered by the first fiber product adjacent thereto.

\* \* \* \* \*